United States Patent [19]

Jensen-Korte et al.

[11] Patent Number: 4,826,867
[45] Date of Patent: May 2, 1989

[54] SUBSTITUTED 1-ARYL-3-TERT.-BUTYL-PYRAZOLES

[75] Inventors: Uta Jensen-Korte, Duesseldorf; Reinhold Gehring, Wuppertal; Otto Schallner, Monheim; Jörg Stetter, Wuppertal; Benedikt Becker, Mettmann; Wolfgang Behrenz, Overath; Wilhelm Stendel, Wuppertal, all of Fed. Rep. of Germany

[73] Assignee: Bayer Aktiengesellschaft, Leverkusen, Fed. Rep. of Germany

[21] Appl. No.: 89,474

[22] Filed: Aug. 25, 1987

[30] Foreign Application Priority Data

Aug. 26, 1986 [DE] Fed. Rep. of Germany ....... 3628892

[51] Int. Cl.$^4$ .................. A01N 43/56; C07D 401/04; C07D 231/16
[52] U.S. Cl. .................................. 514/407; 514/406; 514/341; 546/279; 548/375; 548/376; 548/362
[58] Field of Search ...................... 548/362, 375, 376; 514/406, 407, 341; 546/279

[56] References Cited

U.S. PATENT DOCUMENTS

| 4,146,632 | 3/1979 | Hofer et al. | 548/375 |
| 4,163,052 | 7/1979 | Hofer et al. | 548/377 |
| 4,681,618 | 7/1987 | Gehring et al. | 548/376 |

FOREIGN PATENT DOCUMENTS

| 0201852 | 11/1986 | European Pat. Off. | 548/362 |
| 3623302 | 5/1987 | European Pat. Off. | 546/279 |

OTHER PUBLICATIONS

Burger, "A Guide To The Chemical Basis of Drug Design", 1983, pp. 84–86.
Chemical Abstracts, vol. 106, No. 21, May 25, 1987.
Elguero et al. Bull. Soc. Chim. France (1966) pp. 3727–3743.

*Primary Examiner*—John M. Ford
*Attorney, Agent, or Firm*—Sprung Horn Kramer & Woods

[57] ABSTRACT

Insecticidally and acaricidally active novel 1-aryl-3-tert.-butyl-pyrazoles of the formula

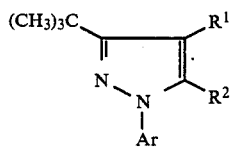

in which
$R^1$ represents nitro or halogen,
$R^2$ represents halogen or the —$NR^3R^4$ group, and also may represent hydrogen when $R^1$ denotes halogen, where
$R^3$ represents hydrogen, in each case optionally substituted alkyl, alkenyl or alkinyl, and in each case optionally substituted cycloalkyl or cycloalkylalkyl and
$R^4$, independently of $R^3$, represents the same radicals as $R^3$, and, in addition, a

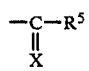

radical, where
X represents oxygen or sulphur and
$R^5$ represents hydrogen, alkyl, alkenyl, alkinyl, halogenoalkyl, alkoxyalkyl, alkylthioalkyl, optionally substituted cycloalkyl, optionally substituted aryl, alkoxy, alkylthio, optionally substituted aryloxy, optionally substituted arylthio, alkylamino, dialkylamino or optionally substituted arylamino; and
Ar represents optionally substituted phenyl, apart from dinitrophenyl, or optionally substituted pyridyl. Intermediates where $R^1$ is replaced by hydrogen are also new and are also pesticidally active.

12 Claims, No Drawings

SUBSTITUTED 1-ARYL-3-TERT.-BUTYL-PYRAZOLES

The present invention relates to new substituted 1-aryl-3-tert.-butyl-pyrazoles, several processes for the preparation thereof, and the use thereof as pesticides, particularly as insecticides and acaricides.

It is already known that certain 5-amino-1-phenyl-pyrazoles which are substituted in the 4-position by a cyano group, such as, for example, 4-cyano-5-propionamido-1-(2,4,6-trichlorophenyl)-pyrazole, have herbicidal properties (cf., for example, DE-OS (German Published Specification) No. 3,226,513).

In addition, it is known that pyrazoles, such as, for example, 5-dimethylaminocarbonyloxy-1-isopropyl-3-methylsulphinylmethylpyrazole or 1-cyclohexyl-5-dimethylaminocarbonyloxy-3-methylthiomethyl-pyrazole, have insecticidal properties (cf. DE-OS (German Published Specification) No. 2,819,932 corresponding to U.S. patent application Ser. No. 31,096 filed Apr. 18, 1979, now U.S. Pat. No. 4,215,132, and DE-OS (German Published Specification) No. 2,839,270.

However, none of these compounds has an insecticidal action which is always completely satisfactory against all harmful insects, particularly at low application amounts or concentrations.

New substituted 1-aryl-3-tert.-butyl-pyrazoles of the general formula (I)

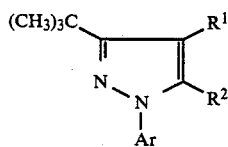 (I)

in which
R$^1$ represents nitro or halogen,
R$^2$ represents halogen or the —NR$^3$R$^4$ group, and also may represent hydrogen when R$^1$ denotes halogen, where
R$^3$ represents hydrogen, in each case optionally substituted alkyl, alkenyl or alkinyl, and in each case optionally substituted cycloalkyl or cycloalkylalkyl and
R$^4$, independently of R$^3$, represents the same radicals as R$^3$, and, in addition, a

radical, where
X represents oxygen or sulphur and R$^5$ represents hydrogen, alkyl, alkenyl, alkinyl, halogenoalkyl, alkoxyalkyl, alkylthioalkyl, optionally substituted cycloalkyl, optionally substituted aryl, alkoxy, alkylthio, optionally substituted aryloxy, optionally substituted arylthio, alkylamino, dialkylamino or optionally substituted arylamino; and
Ar represents optionally substituted phenyl, apart from dinitrophenyl, or optionally substituted pyridyl, have been found.

It has furthermore been found that the new substituted 1-aryl-3-tert.-butyl-pyrazoles of the general formula (I),

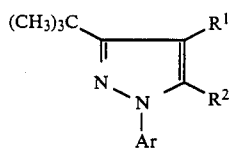 (I)

in which
R$^1$ represents nitro or halogen,
R$^2$ represents halogen or the —NR$^3$R$^4$ group, and also may represent hydrogen when R$^1$ denotes halogen, where
R$^3$ represents hydrogen, in each case optionally substituted alkyl, alkenyl or alkinyl, and in each case optionally substituted cycloalkyl or cycloalkylalkyl, and
R$^4$, independently of R$^3$, represents the same radicals as R$^3$ and, in addition, a

radical, where
X represents oxygen or sulphur, and
R$^5$ represents hydrogen, alkyl, alkenyl, alkinyl, halogenoalkyl, alkoxyalkyl, alkylthioalkyl, optionally substituted cycloalkyl, optionally substituted aryl, alkoxy, alkylthio, optionally substituted aryloxy, optionally substituted arylthio, alkylamino, dialkylamino or optionally substituted arylamino; and
Ar represents optionally substituted phenyl, apart from dinitrophenyl, or optionally substituted pyridyl, are obtained with the aid of the process described below:

(a) the substituted 1-aryl-3-tert.-butyl-pyrazoles of the formula (I),

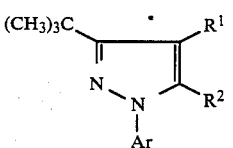 (I)

in which
R$^1$, R$^2$ and Ar have the abovementioned meaning, are obtained when 1-aryl-3-tert.-butyl-pyrazoles of the formula (II),

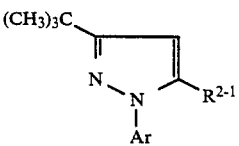 (II)

in which
R$^{2-1}$ represents hydrogen, halogen or the —NR$^3$R$^4$ group, where
R$^3$ and R$^4$ have the abovementioned meaning, and
Ar has the abovementioned meaning, are reacted with halogenating or nitrating agents of the formula (III),

 (III)

in which

R¹ has the abovementioned meaning, and

A represents an electron-withdrawing leaving group, if appropriate in the presence of a diluent and if appropriate in the presence of a catalyst or reaction auxiliary;

(b) substituted 1-aryl-3-tert.-butyl-pyrazoles of the formula (Ia),

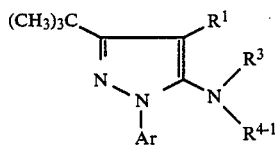

(Ia)

in which

R¹, R³ and Ar have the abovementioned meaning and R⁴⁻¹, independently of R³, represents the same radicals as R³, are obtained when the 1-aryl-5-halogeno-3-tert.-butyl-pyrazoles of the formula (Ib)

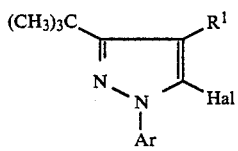

(Ib)

in which

R¹ and Ar have the abovementioned meaning, and

Hal represents halogen, preferably bromine or chlorine, which can be obtained by process (a) are reacted with amines of the formula (IV)

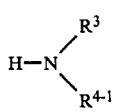

(IV)

in which

R³ and R⁴⁻¹ have the abovementioned meaning, if appropriate in the presence of a diluent and if appropriate in the presence of an acid-binding agent;

(c) substituted 1-aryl-3-tert.-butyl-pyrazoles of the formula (Ic),

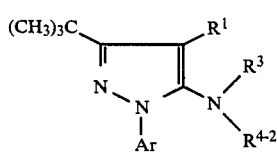

(Ic)

in which

R¹, R³ and Ar have the abovementioned meaning, and

R⁴⁻² represents the abovementioned meanings of R⁴, apart from hydrogen, are obtained when the 5-amino-1-aryl-3-tert.-butyl-pyrazoles of the formula (Id),

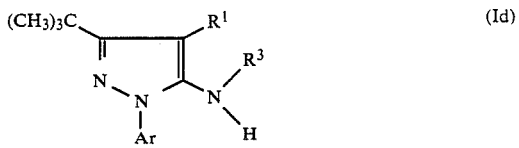

(Id)

in which

R¹, R³ and Ar have the abovementioned meaning, which can be obtained by processes (a) and (b)

(a) are reacted with acylating agents of the formula (V)

(V)

in which

R⁵ and X have the abovementioned meaning, and

A¹ represents halogen or the R⁵—CO—O— radical, where

R⁵ has the abovementioned meaning, or (β) are reacted with alkylating agents of the formula (VI),

(VI)

in which

R⁴⁻² has the abovementioned meaning, and

A² represents an electron-withdrawing leaving group, in each case if appropriate in the presence of a diluent and if appropriate in the presence of an acid-binding agent and if appropriate in the presence of a catalyst;

(d) 5-amino-1-aryl-3-tert.-butyl-pyrazoles of the formula (Id),

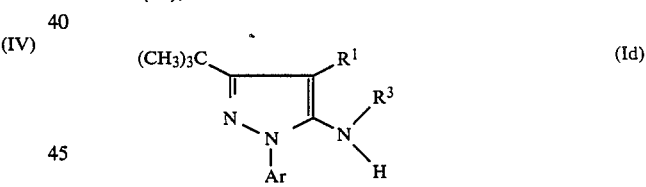

(Id)

in which

R¹, R³ and Ar have the abovementioned meaning, are also obtained when the 1-aryl-3-tert.-butyl-pyrazoles of the formula (Ie),

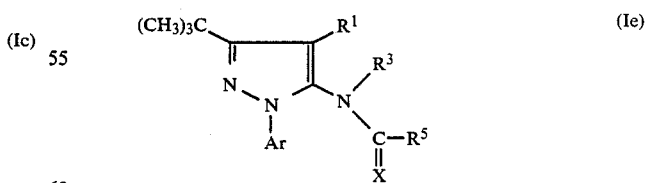

(Ie)

in which

R¹, R³, R⁵, X and Ar have the abovementioned meaning, which can be obtained by processes (a) or (c) are deacylated, if appropriate in the presence of a diluent and if appropriate in the presence of a catalyst;

(e) 1-aryl-3-tert.-butyl-pyrazoles of the formula (If),

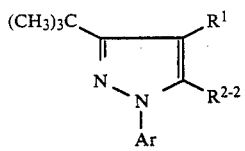

(If)

in which
R¹ and Ar have the abovementioned meaning, and
R²⁻² represents halogen, and also represents hydrogen when R¹ denotes halogen,
are obtained when the 5-amino-1-aryl-3-tert.-butyl-pyrazoles of the formula (Ig)

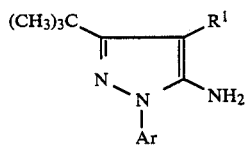

(Ig)

in which
R¹ and Ar have the abovementioned meaning, which can be obtained by processes (a), (b) or (d) are reacted with an inorganic or organic nitrite in the presence of a reaction auxiliary and in the presence of a hydrohalic acid and if appropriate in the presence of a diluent.

Finally, it has been found that the new 1-aryl-3-tert.-butyl-pyrazoles of the general formula (I) have strong insecticidal and acaricidal properties.

Surprisingly, the 1-aryl-3-tert.-butyl-pyrazoles of the general formula (I) according to the invention exhibit a considerably better insecticidal and acaricidal activity than the pyrazole derivatives which are known from the state of the art, such as, for example, 4-cyano-5-propionamido-1-(2,4,6-trichlorophenyl)-pyrazole, 5-dimethylaminocarbonyloxy-1-isopropyl-3-methylsulphinylmethyl-pyrazole or 1-cyclohexyl-5-dimethylaminocarbonyloxy-3-methylthiomethyl-pyrazole, which are similar compounds chemically and regarding their action.

The formula (I) provides a general definition of the new substituted 1-aryl-3-tert.-butyl-pyrazoles. In this formula, R¹ preferably represents nitro, fluorine, chlorine, bromine or iodine;

R² preferably represents fluorine, chlorine, bromine, iodine or the —NR³R⁴ group; and also may represent hydrogen when R¹ represents a halogen, where R³ represents hydrogen or, in each case straight-chain or branched, alkyl, alkenyl and alkinyl, in each case having up to 8 carbon atoms, which are optionally monosubstituted or polysubstituted, where the substituents are identical or different and suitable substituents are in each case: halogen, cyano, nitro, hydroxyl, mercapto, carboxyl, in each case straight-chain or branched alkoxy, alkylthio and alkoxycarbonyl, in each case having up to 6 carbon atoms; furthermore represents cycloalkyl having 3 to 7 carbon atoms and cycloalkylalkyl having 3 to 7 carbon atoms in the cycloalkyl part and 1 to 4 carbon atoms in the alkyl part which are in each case optionally monosubstituted or polysubstituted, the substituents being identical or different and suitable substituents in the cycloalkyl part being in each case: halogen and straight-chain or branched alkyl having 1 to 4 carbon atoms; and R⁴, independently of R³, represents the same radicals as R³, and, in addition, a —C(X)—R⁵ radical, where X represents oxygen or sulphur, and R⁵ represents hydrogen, straight-chain or branched alkyl having 1 to 12 carbon atoms, in each case straight-chain or branched alkenyl or alkinyl, in each case having 2 to 4 carbon atoms, in each case straight-chain or branched alkoxyalkyl, alkylthioalkyl, alkoxy, alkylthio, alkylamino, dialkylamino or halogenoalkyl in each case having 1 to 4 carbon atoms in the individual alkyl parts and, in the case of halogenoalkyl, having up to 9 identical or different halogen atoms, in addition cycloalkyl, having 3 to 7 carbon atoms, which is optionally monosubstituted or polysubstituted by halogen, C₁–C₄-alkyl or C₁–C₄-halogenoalkyl, the substituents being identical or different, and phenyl, phenoxy, phenylthio or phenylamino which is in each case optionally monosubstituted or polysubstituted, the substituents being identical or different and suitable phenyl substituents being in each case: halogen, in each case straight-chain or branched alkyl or alkoxy in each case having 1 to 4 carbon atoms, and halogenoalkyl having 1 to 4 carbon atoms and 1 to 9 identical or different halogen atoms; and Ar preferably represents phenyl (apart from dinitrophenyl), 2-pyridyl, 3-pyridyl or 4-pyridyl which is in each case optionally monosubstituted or polysubstituted, the substituents being identical or different and suitable substituents being in each case: halogen, cyano, nitro, in each case straight-chain or branched alkyl, alkoxy or alkoxycarbonyl in each case having 1 to 4 carbon atoms in the alkyl parts, in each case straight-chain or branched halogenoalkyl or halogenoalkoxy in each case having 1 to 4 carbon atoms and 1 to 9 identical or different halogen atoms, or an —S(O)$_m$—R⁶ radical, where R⁶ represents amino, in each case straight-chain or branched alkyl, alkylamino, dialkylamino or halogenoalkyl in each case having 1 to 4 carbon atoms in the individual alkyl parts, and, in the case of halogenoalkyl, having 1 to 9 identical or different halogen atoms, and m represents a number 0, 1 or 2.

Particularly preferred substituted 1-aryl-3-tert.-butyl-pyrazoles of the formula (I) are those in which:

R¹ represents nitro, chlorine or bromine;

R² represents chlorine, bromine or the —NR³R⁴ group; and also may represent hydrogen when R¹ represents a halogen, where R³ represents methyl, ethyl, n- or i-propyl, n-, i-, s- or t-butyl, allyl, butenyl, propargyl or butinyl which is in each case optionally mono- to trisubstituted, the substituents being identical or different and suitable substituents being: fluorine, chlorine, bromine, iodine, cyano, nitro, hydroxyl, mercapto, carboxyl, methoxy, ethoxy, n- or i-propoxy, methylthio, ethylthio, n- or i-propylthio, methoxycarbonyl, ethoxycarbonyl, n-or i- propoxycarbonyl, n-, i-, s- or t-butoxycarbonyl; furthermore represents cyclopropyl, cyclopropylmethyl, cyclopentyl, cyclopentylmethyl, cyclohexyl, cyclohexylmethyl, cyclohexylethyl, cycloheptyl or cycloheptylmethyl which is in each case optionally mono- to trisubstituted in the cycloalkyl part, the substituents being identical or different;

R⁴, independently of R³, represents the same radicals as R³, and, in addition, a

radical where

X represents oxygen or sulphur, and
R⁵ represents hydrogen, methyl, ethyl, n- or i-propyl, n-, i-, s- or t-butyl, undecyl, vinyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 3-chloropropyl or heptafluoro-n-propyl, represents cyclopropyl, cyclopentyl or cyclohexyl which is in each case optionally mono- to tetrasubstituted by fluorine, chlorine, bromine, methyl or trifluoromethyl, the substituents being identical or different, and represents phenyl, phenoxy, phenylthio or phenylamino which is in each case optionally mono- to trisubstituted by methyl, methoxy, chlorine or trifluoromethyl, the substituents being identical or different; and Ar represents phenyl (apart from dinitrophenyl) which is optionally mono- to pentasubstituted, the substituents being identical or different, or represents 2-pyridyl, 3-pyridyl or 4-pyridyl, which is in each case optionally mono- to tetrasubstituted the substituents being identical or different and suitable substituents being in each case: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an —S(O)ₘ—R⁶ radical, where R⁶ represents amino, methylamino, ethylamino, dimethylamino, diethylamino, fluorodichloromethyl, difluoromethyl, tetrafluoroethyl, trichloroethyl, trifluoromethyl, difluorochloromethyl, methyl or ethyl and m represents a number 0, 1 or 2.

In addition to the compounds mentioned in the preparation examples, the following substituted 1-aryl-3-tert.-butyl-pyrazoles of the general formula (I) may be mentioned individually:

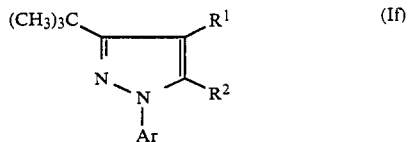

(If)

| R¹ | R² | Ar |
|---|---|---|
| Br | H | 4-Cl, 3-OCF₃-phenyl |
| Cl | H | 4-Cl, 3-OCF₃-phenyl |
| NO₂ | —NH₂ | 3,5-dichloro-pyridyl |
| NO₂ | —NHCH₃ | 2,6-dichloro-4-CF₃-phenyl |
| NO₂ | —NHCH₂CH₂OCH₃ | 2,6-dichloro-4-CF₃-phenyl |
| Br | —N(CH₃)₂ | 2,6-dichloro-4-CF₃-phenyl |
| NO₂ | —NHCH₂CH₂C(O)OC₂H₅ | 2,6-dichloro-4-CF₃-phenyl |
| NO₂ | Br | 3,5-dichloro-pyridyl |
| NO₂ | Cl | 3-Cl, 5-OCF₃-pyridyl |

-continued

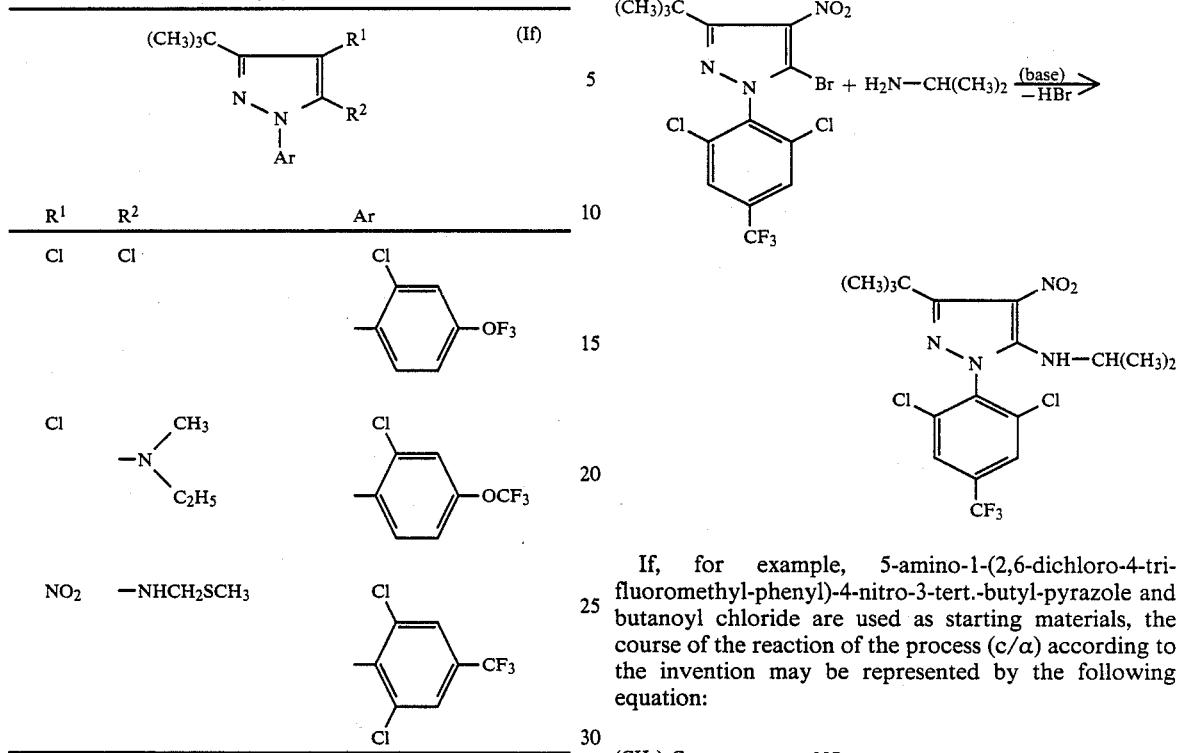

| R¹ | R² | Ar |
|---|---|---|
| Cl | Cl | 2-Cl, 4-OF₃ phenyl |
| Cl | -N(CH₃)(C₂H₅) | 2-Cl, 4-OCF₃ phenyl |
| NO₂ | -NHCH₂SCH₃ | 2,5-Cl, 4-CF₃ phenyl (Cl,Cl,CF₃) |

If, for example, 1-(2,6-dichloro-4-trifluoromethyl-phenyl)-5-propionamido-3-tert.-butyl-pyrazole and nitric acid are used as starting materials, the course of the reaction of the process (a) according to the invention may be represented by the following equation:

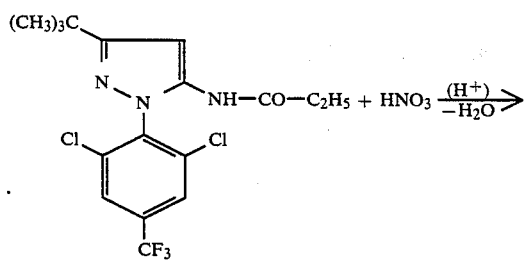

If, for example, 5-bromo-1-(2,6-dichloro-4-trifluoromethyl-phenyl)-4-nitro-3-tert.-butyl-pyrazole and isopropylamine are used as starting materials, the course of the reaction of the process (b) according to the invention may be represented by the following equation:

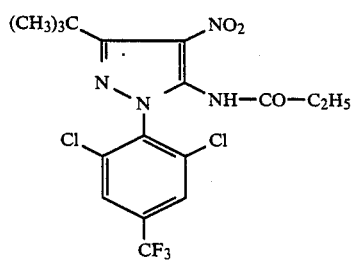

If, for example, 5-amino-1-(2,6-dichloro-4-trifluoromethyl-phenyl)-4-nitro-3-tert.-butyl-pyrazole and butanoyl chloride are used as starting materials, the course of the reaction of the process (c/α) according to the invention may be represented by the following equation:

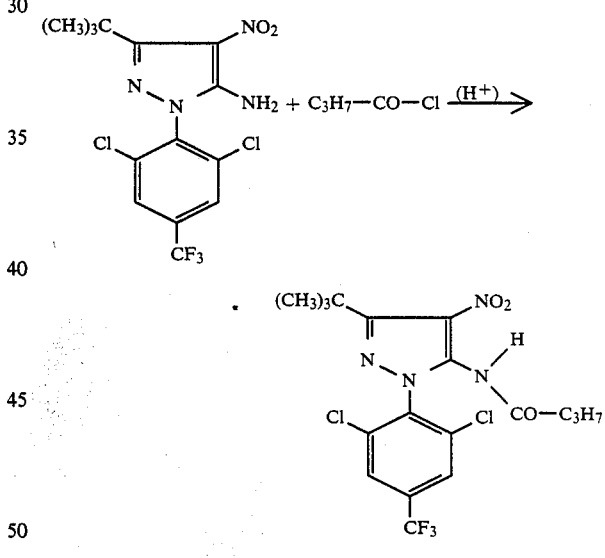

If, for example, 5-amino-1-(2,6-dichloro-4-trifluoromethyl-phenyl)-4-nitro-3-tert.-butyl-pyrazole and dimethyl sulphate are used as starting materials, the course of the reaction of the process (c/β) according to the invention may be represented by the following equation:

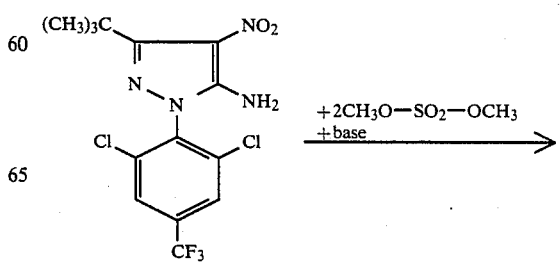

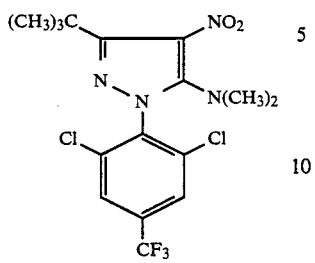

If, for example, 5-acetylamino-4-chloro-1-(2,6-dichloro-4-trifluoromethyl-phenyl)-3-tert.-butyl-pyrazole is used as starting material, the course of the reaction of the process (d) according to the invention may be represented by the following equation:

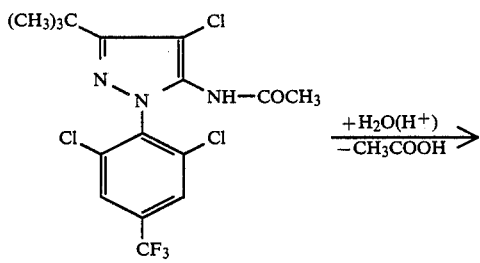

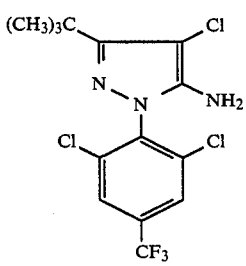

If, for example, 5-amino-1-(2,6-dichloro-4-trifluoromethyl-phenyl)-4-nitro-3-tert.-butyl-pyrazole and tert.-butyl nitrite/bromoform are used as starting materials, the course of the reaction of the process (e) according to the invention may be represented by the following equation:

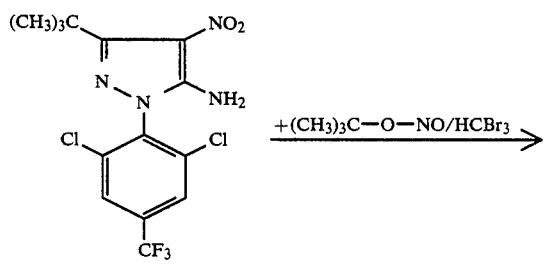

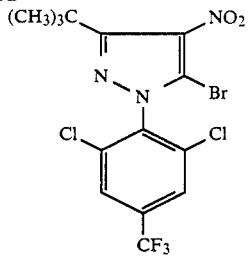

The formula (II) provides a general definition of the 1-aryl-3-tert.-butyl-pyrazoles which are required as starting materials for carrying out the process (a) according to the invention. In this formula, Ar preferably represents those radicals which have already been mentioned in connection with the description of the substances of the formula (I) according to the invention as being preferred for this substituent. $R^{2-1}$ preferably represents hydrogen, fluorine, chlorine, bromine, iodine and the $-NR^3R^4$ group, $R^3$ and $R^4$ preferably representing those radicals which have already been mentioned in connection with the description of the substances of the formula (I) according to the invention as being preferred for these substituents.

The 1-aryl-3-tert.-butyl-pyrazoles of the formula (II) were hitherto not known; however, they can be obtained in a generally known fashion. The compounds of formula (II) also exhibit insecticidal effectiveness.

1-Aryl-3-tert.-butyl-pyrazoles of the formula (IIa),

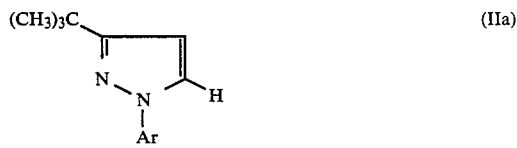

in which
Ar has the abovementioned meaning, are obtained, for example, when (2,2-dimethoxy)-ethyl tert.-butyl ketone of the formula (VII), $$(CH_3)_3C-CO-CH_2CH(OCH_3)_2 \qquad (VII)$$

is cyclized using hydrazines of the formula (VIII),

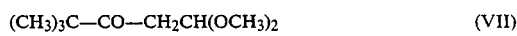

in which
Ar has the abovementioned meaning, if appropriate in the presence of a diluent, such as, for example, ethylene glycol monoethyl ether or ethanol, at temperatures between $-50°$ C. and $+150°$ C. (in this respect, cf. also German patent application No. P 3,509,567 of 16.03.1985 corresponding to U.S. patent application Ser. No 836,268 filed Mar. 4, 1986, now pending.

(2,2-Dimethoxy)-ethyl tert.-butyl ketone of the formula (VIII) is known (cf. Chemistry Letters 1978, p. 263).

Most of the hydrazines of the formula (VIII) are known or can be prepared in an analogous fashion by known processes (cf., for example, Houben-Weyl, Methoden der organischen Chemie [Methods of organic chemistry]; volume X/2, p. 203, Thieme Verlag, Stuttgart 1967).

1-Aryl-5-halogeno-3-tert.-butyl-pyrazoles of the formula (IIb),

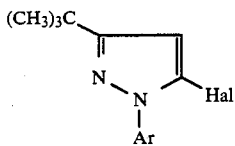

in which

Ar and Hal have the abovementioned meaning, are obtained, for example, when pyrazolin-5-ones of the formula (IX),

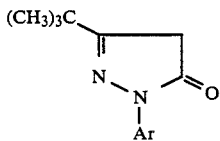

in which

Ar has the abovementioned meaning, are reacted with phosphorus oxyhalides at temperatures between 100° and 250° C. (cf. also German patent application No. P 3,520,329 of 07.06.1985, corresponding to U.S. patent application Ser. No. 866,050 filed May 22, 1986, now pending.

The pyrazolin-5-ones of the formula (IX) are obtained by cyclizing methyl tert.-butyl-carbonyl-acetate using hydrazines of the formula (VIII), if appropriate in the presence of a diluent, such as, for example, toluene or ethanol, and if appropriate in the presence of a catalyst, such as, for example, p-toluenesulfonic acid, at temperatures between +50° C. and +150° C.

5-Amino-1-aryl-3-tert.-butyl-pyrazoles of the formula (IIc),

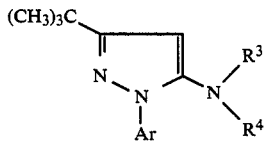

in which

Ar, $R^3$ and $R^4$ have the abovementioned meaning, are obtained, for example, when 5-amino-1-aryl-3-tert.-butyl-pyrazoles of the formula (IIe),

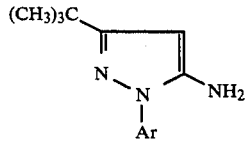

in which

Ar has the abovementioned meaning, are reacted with acylating agents of the formula (V) or with alkylating agents of the formula (VI), corresponding to the process (c) according to the invention.

The 5-amino-1-aryl-3-tert.-butyl-pyrazoles of the formula (IIe) can be obtained when cyanopinacolin [$(CH_3)_3C-CO-CH_2CN$; cf. Ber. 44, 2065 (1911)] are cyclized using hydrazines of the formula (VIII), if appropriate in the presence of a diluent, such as, for example, ethylene glycol monoethyl ether or ethanol, at temperatures between +50° C. and +150° C.

The formula (III) provides a general definition of the halogenating or nitrating agents which are additionally required as starting materials for carrying out the process (a) according to the invention. In this formula, $R^1$ preferably represents those radicals which have already been mentioned in connection with the description of the substances of the formula (I) according to the invention as being preferred for this substituent. A preferably represents halogen, particularly chlorine or bromine. Electrophilic reagents which can furthermore be used are sulphuryl chloride, phosphorus oxychloride, nitrating acid and other nitrating agents which are conventionally to be used.

The halogenating and nitrating agents of the formula (III) are generally known compounds of organic chemistry.

The formula (Ib) provides a general definition of the 1-aryl-5-halogeno-3-tert.-butyl-pyrazoles which are required as starting materials for carrying out the process (b) according to the invention. In this formula, Ar and $R^1$ preferably represent those radicals which have already been mentioned in connection with the description of the substances of the formula (I) according to the invention as being preferred for these substituents. Hal preferably represents bromine or chlorine.

The 1-aryl-5-halogeno-3-tert.-butyl-pyrazoles of the formula (Ib) are compounds according to the invention and can be obtained with the aid of the process (a) according to the invention.

The formula (IV) provides a general definition of the amines which are additionally required as starting materials for carrying out the process (b) according to the invention. In this formula, $R^3$ preferably represents those radicals which have already been mentioned in connection with the description of the substances of the formula (I) according to the invention as being preferred for this substituent, $R^{4-1}$, independently of $R^3$, preferably represents the same radicals as $R^3$.

The amines of the formula (IV) are generally known compounds of organic chemistry.

The formula (Id) provides a general definition of the 5-amino-1-aryl-3-tert.-butyl-pyrazoles which are required as starting materials for carrying out the process (c) according to the invention. In this formula, Ar, $R^1$ and $R^3$ preferably represent those radicals which have already been mentioned in connection with the description of the substances of the formula (I) according to the invention as being preferred for these substituents.

The 5-amino-1-aryl-3-tert.butyl-pyrazoles of the formula (Id) are compounds according to the invention and can be obtained with the aid of the processes (a) and (b) according to the invention.

The formula (V) provides a general definition of the acylating agents which are additionally required as starting materials for carrying out the process (c)/version α according to the invention. In this formula, $R^5$ and X preferably represent those radicals which have already been mentioned in connection with the description of the substances of the formula (I) according to the invention as being preferred for these substituents. $A^1$ preferably represents chlorine or bromine or an $R^5-CO'O-$radical.

The formula (VI) provides a general definition of the alkylating agents which are additionally required as starting materials for carrying out the process (c)/version β according to the invention. In this formula, $R^{4-2}$ preferably represents those radicals which have already been mentioned in connection with the description of the substances of the formula (I) according to the invention as being preferred for $R^4$, apart from hydrogen. $A^2$ preferably represents chlorine, bromine or iodine, and in each case optionally substituted alkylsulphonyloxy, alkoxysulphonyloxy or arylsulphonyloxy, such as, for example, methoxysulphonyloxy or p-tolylsulphonyloxy.

The acylating agents of the formula (V) and the alkylating agents of the formula (VI) are generally known compounds of organic chemistry.

The formula (Ie) provides a general definition of the 1-aryl-3-tert.-butyl-pyrazoles which are required as starting materials for carrying out the process (d) according to the invention. In this formula, $R^1$, $R^3$, $R^5$, X and Ar preferably represent those radicals which have already been mentioned in connection with the description of the substances of the formula (I) according to the invention as being preferred for these substituents.

The 1-aryl-3-tert.-butyl-pyrazoles of the formula (Ie) are compounds according to the invention and can be obtained with the aid of the processes (a) and (c) according to the invention.

The formula (Ig) provides a general definition of the 5-amino-1-aryl-3-tert.-butyl-pyrazoles which are required as starting materials for carrying out the process (e) according to the invention. In this formula, $R^1$ and Ar preferably represent those radicals which have already been mentioned in connection with the description of the substances of the formula (I) according to the invention as being preferred for these substituents.

The 5-amino-1-aryl-3-tert.-butyl-pyrazoles of the formula (Ig) are compounds according to the invention and can be obtained with the aid of the processes (a), (b) or (d) according to the invention.

Suitable diluents for carrying out the process (a) according to the invention are all solvents which can conventionally be used for such electrophilic substitution. The acids or mixtures, such as, for example, sulphuric acid, nitric acid, sulphuryl chloride, phosphorus oxychloride/dimethylformamide or nitric acid, which are suitable as reagents are preferably used simultaneously as diluents. If appropriate, inert organic solvents, such as, for example, glacial acetic acid or chlorinated hydrocarbons, such as methylene chloride, chloroform or carbon tetrachloride, are also suitable as diluents.

Suitable catalyst or reaction auxiliaries for carrying out the preparation process (a) are likewise the catalysts which are conventional for such reactions; acidic catalysts, such as, for example, sulphuric acid, iron-III chloride or other Lewis acids, or acetic anhydride, are preferably used.

The reaction temperatures may be varied within a relatively wide range when carrying out the preparation process (a). In general, the process is carried out at temperatures between $-50°$ C. and $+200°$ C., preferably between $-20°$ and $+150°$ C.

To carry out the preparation process (a), 1.0 to 10.0 moles, preferably 1.0 to 5.0 moles, of electrophilic agent of the formula (III) and, if appropriate, 0.1 to 10 moles of catalyst or reaction auxiliary are generally employed per mole of 1-aryl-3-tert.-butyl-pyrazole of the formula (II). The reaction is carried out and the reaction products of the formula (I) are worked up and isolated in a generally conventional fashion.

Suitable diluents for carrying out the process (b) according to the invention are inert organic solvents. These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, ketone, such as acetone or butanone, nitriles, such as acetonitrile or propionitrile, amides, such as dimethylformamide dimethylacetamide, N-methylformanilide, N-methylpyrrolidone or hexamethylphosphoric triamide, esters, such as ethyl acetate, or sulphoxides, such as dimethyl sulphoxide.

The process (b) according to the invention may, if appropriate, be carried out in the presence of a suitable acid-binding agent.

Suitable as such are all conventional inorganic or organic bases. These include, for example, alkali metal hydroxides, such as sodium hydroxide or potassium hydroxide, alkali metal carbonates, such as sodium carbonate, potassium carbonate or sodium hydrogen carbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

However, it is also possible to use an appropriate excess of the amine of the formula (IV) employed as reactant simultaneously as acid-binding agent.

The reaction temperatures may be varied within a relatively wide range when carrying out the process (b) according to the invention. In general, the process is carried out at temperatures between $-20°$ C. and $+200°$ C., preferably at temperatures between $0°$ C. and $+150°$ C.

To carry out the process (b) according to the invention, 1.0 to 10.0 moles, preferably 1.0 to 5.0 moles, of amine of the formula (IV) are generally employed per mole of 1-aryl-5-halogeno-3-tert.-butyl-pyrazole of the formula (Ib). The reaction is carried out and the reaction products of the formula (Ia) are worked up and isolated by generally conventional methods.

Suitable diluents for carrying out the process (c) according to the invention are inert organic solvents. These include, in particular, aliphatic or aromatic, optionally halogenated hydrocarbon, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, ketones, such as acetone or butanone, nitriles such as acetonitrile or propionitrile and amides, such as dimethylformamide, dimethylacetamide, N-methylformanilide, N-methylpyrrolidone or hexamethylphosphoric triamide, esters, such as ethyl acetate, or sulphoxides such as dimethyl sulphoxide.

If appropriate, the process (c) according to the invention may also be carried out in a two-phase system, such as, for example, water/toluene or water/dichloromethane, if appropriate in the presence of a phase-transfer catalyst. Examples of such catalysts which may be mentioned are: tetrabutylammonium iodide, tetrabutylammonium bromide, tributyl-methylphosphonium bromide, trimethyl-$C_{13}$/$C_{15}$-alkylammonium chloride dibenzylmethylammonium sulphate, dimethyl-$C_{12}$/$C_{14}$-alkyl-benzylammonium chloride, tetrabutylammonium hydroxide, 15-crown-5, 18-crown-6, triethylbenzylammonium chloride and trimethylbenzylammonium chloride.

Suitable acid-binding agents for carrying out the preparation process (c) are all inorganic and organic bases which may conventionally be used. Alkali metal hydrides, hydroxides, amides, alcoholates, carbonates or hydrogen carbonates, such as, for example, sodium hydride, sodium amide, sodium methylate, sodium hydroxide, sodium carbonate or sodium hydrogen carbonate, or alternatively tertiary amines, such as, for example, triethylamine, N,N-dimethylaniline, pyridine, 4-(N,N-dimethylamino)pyridine, diazabicyclooctane (DABCO), diazabicyclononene (DBN) or diazabicycloundecene (DBU) are preferably used.

The reaction temperatures may be varied within a relatively wide range when carrying out the preparation process (c). In general, the process is carried out at temperatures between −20° C. and +150° C., preferably between 0° C. and +100° C.

To carry out the preparation process (c), 1.0 to 20.0 moles, preferably 1.0 to 15.0 moles, of acylating agent of the formula (V) or of alkylating agent of the formula (VI) and, if appropriate, 1.0 to 3.0 moles, preferably 1.0 to 2.0 moles, of acid-binding agent and, if appropriate, 0.01 to 1.0 mole of phase-transfer catalyst are generally employed per mole of 5-amino-1-aryl-3-tert.-butyl-pyrazole of the formula (Id). The reaction is carried out and the reaction products of the formula (Ic) are worked up and isolated in a generally conventional fashion.

Suitable diluents for carrying out the process (d) according to the invention are inorganic or organic polar solvents. Alcohols, such as, for example, methanol, ethanol or propanol, or mixtures thereof with water are preferably used.

Suitable catalysts for carrying out the preparation process (d) are preferably acid, particularly hydrochloric acid or sulphuric acid, and bases, particularly sodium hydroxide, sodium hydride and potassium tert.-butylate.

The reaction temperatures may be varied within a relatively wide range when carrying out the preparation process (d). In general, the process is carried out at temperatures between +20° C. and +150° C., preferably between +50° C. and +120° C.

To carry out the preparation process (d), 1.0 to 20.0 moles, preferably 1.0 to 10.0 moles, of catalyst are generally employed per mole of 1-aryl-3-tert.-butyl-pyrazole of the formula (Ie), and the mixture is warmed for several hours at the reaction temperature necessary. The reaction products of the formula (Id) are worked up, isolated and purified by conventional methods.

The process (e) according to the invention is carried out in the presence of an inorganic or organic nitrite. Suitable as such are all nitrite compounds which are usually conventional for such diazotization reactions. Alkali metal nitrites, such as, for example, sodium nitrite, or alkyl nitrites, such as, for example, t-butyl nitrite, or isopentyl nitrite, are particularly preferably used.

The process (e) according to the invention is carried out in the presence of a hydrohalic acid. In this case, 1-aryl-pyrazoles of the formula (If), in which the $R^{2-2}$ radical represents a halogen radical which corresponds to the anion of the hydrohalic acid used, are obtained as reaction products. In each case aqueous or alternatively non-aqueous solutions of hydrofluoric acid, hydrochloric acid, hydrobromic acid or hydroiodic acid are preferably used.

Suitable diluents for carrying out the process (e) according to the invention are all solvents which are usually conventional for such diazotization reactions. Halogenated hydrocarbons, such as chloroform or bromoform, or aqueous acids, such as, for example, hydrohalic acids or sulphuric acid, are preferably used, the acid component simultaneously functioning as a reagent and/or as a reaction auxiliary. When bromoform is used as diluent, the corresponding 5-bromo-pyrazoles are generally obtained, bromoform functioning simultaneously as diluent and as a reagent. The corresponding reaction in the presence of chloroform as diluent generally yields a mixture of 5-chloro-pyrazole compounds of the formula (If) and the analogously reduced compounds of the formula (If) which carry a hydrogen radical in the 5-position of the pyrazole ring. These mixtures can be separated by conventional separation methods, such as, for example, distillatively or chromatographically.

The process (e) according to the invention is conventionally carried out in the presence of a reaction auxiliary. Suitable as such are, in particular, strong mineral acids, such as sulphuric acid or phosphoric acid, or the abovementioned hydrohalic acid, which, in this case, simultaneously function as a reagent and as a catalyst.

The process (e) according to the invention may, if appropriate, be carried out in the presence of a suitable reducing agent. In this case, 1-aryl-pyrazoles of the formula (If), in which the $R^{2-2}$ radical represents hydrogen, are obtained. In these case, hypophosphorous acid ($H_3PO_2$) is particularly preferably used as reducing agent.

The reaction temperatures may be varied within a relatively wide range when carrying out the process (e) according to the invention. In general, the process is carried out at temperatures between −30° C. and +60° C., preferably at temperatures between −°° C. and +40° C.

To carry out the process (e) according to the invention, 1.0 to 1.8 moles of nitrite, if appropriate 1.0 to 20.0 moles, preferably 1.0 to 10.0 moles, of hydrohalic acid, if appropriate 1.0 to 50.0 moles, preferably 1.0 to 20.0 moles, of reducing agent and if appropriate 1.0 to 20.0 moles, preferably 1.0 to 10.0 moles, of mineral acid which is used as reaction auxiliary are generally employed per mole of 5-amino-1-aryl-3-tert.-butyl-pyrazole of the formula (Ig).

In this process, the nitrite, if appropriate dissolved in a suitable diluent, is conventionally added in small portions to the reaction mixture, comprising 5-amino-1-aryl-3-tert.-butyl-pyrazole of the formula (Ig), mineral acid, diluent and hydrohalic acid or reducing agent.

The reaction products of the formula (If) are worked up and isolated by conventional methods, for example by filtering off crystalline products or by extraction with a suitable organic solvent. Identification is effected by means of the melting point or by the proton nuclear magnetic resonance spectrum.

The active compounds are suitable for combating animal pests, in particular insects, arachnida and nematodes, which are encountered in agriculture, in forestry, in the protection of stored products and of materials, and in the hygiene field and are well tolerated by plants and have a favorable toxicity towards warm-blooded animals. Thy are active against normally sensitive and resistant specie and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientals, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. from the order of the Thysanoptera, for example, *Hercinothrips femoralis* and *Thrips tabaci.* From the order of the Heteroptera, for example, Eurygaster spp.,*Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus, ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., Earias insulana, Heliothis spp., *Laphygma exigua, Mamestra brassicae, Panolis flammea, Prodenia litura,* Spodoptera spp., Trichoplusiani, Caprocapsa pomonella, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochlearine,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, Xenopsylla cheopis and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes, spp., Sarcoptes spp., Tarsonemus spp., *Bryobia praetiosa,* Panonychus spp. and Tetranychus spp.

The active compounds according to the invention are not only active against plant, hygiene and stored-product pests, but also, in the veterinary medicine sector, against animal parasites (ectoparasites), such as scaly ticks, argasidae, scab mites, trombidae, flies (stinging and sucking), parasitic fly larvae, lice, hair lice, bird lice and fleas. They are active against normally sensitive and resistant species and strains, as well as against all parasitic and non-parasitic stages of development of the ectoparasites.

The active compounds according to the invention are distinguished by a strong insecticidal and acaricidal activity. They can be used particularly successfully against insects which damage plants, such as, for example, against the larvae of the mustard beetle (*Phaedon cochleariae*), and against midges which damage plants, such as, for example, against the common spider mite (*Tetranychus urticae*).

In addition, the active compounds according to the invention have a strong action against hygiene and stored-product pests, and can be used, for example, for combating the housefly (*Musca domestica*), for combating the common granary weevil (*Sitophilus granarius*), or for combating the German cockroach (*Blatella germanica*). In addition, the active compounds according to the invention can be used particularly successfully for combating pests which live parasitically on warm-blooded animals, such as, for example, against faceflies (*Musca autumnalis*) or against stable flies (*Stomoxys calcitrans*). In addition, the active compounds according to the invention also have a good fungicidal activity when applied in appropriate amounts and can be employed, for example, for combating Oomycetes species.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible for use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds which can be used according to the invention are also suitable for combating insects, midges, ticks etc. in the sectors of animal husbandry and cattle breeding; better results, for example higher milk production, greater weight, more attractive animal pelt, longer liffe etc., can be achieved by combating the pests.

The administration of the active compounds which can be used according to the invention occurs in this sector in a known fashion, such as by oral administration in the form of, for example, tablets, capsules, potions, granules, by means of dermal or external administration in the form of, for example, dipping, spraying, pouring-on, spotting-on and dusting, as well as by means of parenteral administration in the form, for example, of injection, and, furthermore, by means of the feed-through process. In addition, administration as molded articles (collar, ear tag) is also possible.

PREPARATION EXAMPLES

Example 1

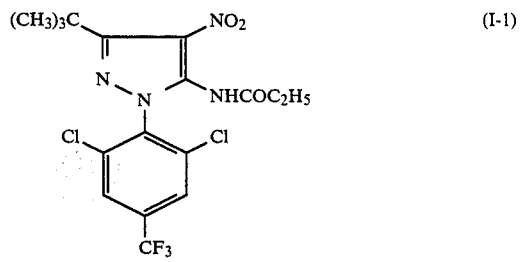

(Process a)

14.2 g (0.225 mole) of 98% strength nitric acid are added dropwise at room temperature to a suspension of 61.2 g (0.15 mole) of 3-tert.-butyl-5-propionamido-1-(2,6-dichloro-4-trifluoromethylphenyl)-pyrazole in 500 ml of acetic anhydride, the temperature increasing to 40° C. The reaction mixture is stirred overnight at room temperature and subsequently poured into ice water. The product which crystallizes out is filtered off under suction, triturated with petroleum ether and dried.

56.2 g (94.4% of theory) of 3-tert.-butyl-4-nitro-5-propionamido-1-(2,6-dichloro-4-trifluoromethylphenyl)-pyrazole of melting point 151°-152° C. are obtained.

Preparation of the starting compound

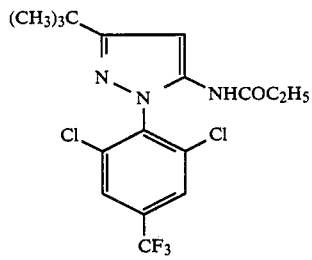
(II-1)

31.4 g (0.34 mole) of propionyl chloride are added dropwise to a solution of 119.5 g (0.34 mole) of 3-tert.-butyl-5-amino-1-(2,6-dichloro-4-trifluoromethyl-phenyl)-pyrazole and 30 g (0.38 mole) of pyridine in 500 ml of dry methylene chloride. The reaction solution is stirred at room temperature and then washed 3 times with 2N HCl, once with water, twice with saturated sodium hydrogen carbonate solution and once with water, dried over magnesium sulphate and concentrated.

After recrystallization from cyclohexane/toluene, 120.7 g (87% of theory) of 3-tert.-butyl-5-propionamido-1-(2,6-dichloro-4-trifluoromethylpheny)-pyrazole of melting point 193° C. are obtained.

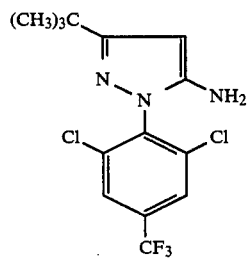
(II-2)

122.5 g (0.5 mole) of 2,6-dichloro-4-trifluoromethyl-phenyl hydrazine and 68.8 g (0.55 mole) of 1-cyano-3,3-dimethyl-2-butanone are dissolved in 1 liter of ethanol and heated for 24 hours at the boiling temperature. 5 ml of concentrated sulphuric acid are subsequently added, and the mixture is stirred for a further 12 hours under reflux. When the reaction is complete, the solvent is removed by distillation, and the residue is taken up in chloroform and rendered alkaline using 25% strength aqueous ammonia solution. The organic phase is separated off and the aqueous phase is extracted with chloroform. The combined organic phases are dried over magnesium sulphate and freed of solvent in vacuo.

105. 6 g (60% of theory) of 5-amino-1-(2,6-dichloro-4-trifluoromethylphenyl)-3-tert.-butyl-pyrazole of melting point 110°-120° C. are obtained.

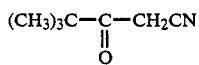

A solution of 108.1 g (1.66 mole) of potassium cyanide in 270 of water is added dropwise to a solution of 201.8 g (1.5 mole) of 1-chloro-3,3-dimethyl-2-butanone and 800 ml of ethanol at the boiling temperature, and the mixture is refluxed for 1 hour. The solvent is subsequently stripped off, and the residue is slurried in 1.5 liters of ice water, dissolved by adding 66.4 g (1.5 mole) of sodium hydroxide, and washed with ether. The aqueous phase is acidified with cooling in ice, extracted with methylene chloride, dried over magnesium sulphate and concentrated.

After recrystallization from ethyl acetate/ligroin, 139.6 g (74.5% of theory) of 1-cyano-3,3-dimethyl-2-butanone of melting point 67°-69° C. are obtained.

Example 2

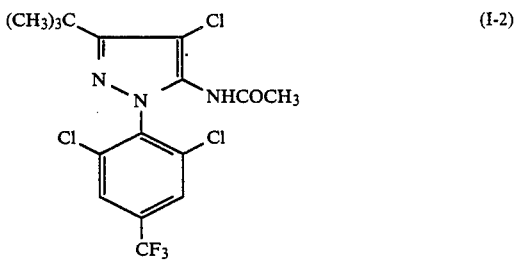
(I-2)

(Process a)

8.9 g (0.066 mole) of sulphuryl chloride in 20 ml of absolute methylene chloride are added dropwise to 23.6 g (0.06 mole) of 3-tert.-butyl-5-acetamido-1-(2,6-dichloro-4-trifluoromethylphenyl)-pyrazole in 250 ml of absolute methylene chloride at room temperature. Stirring is contained overnight, and the reaction mixture is then concentrated to half the volume and the precipitated product is filtered off under suction.

After drying, 22.5 g (87.5% of theory) of 3-tert.-butyl-4-chloro-5-acetamido-1-(2,6-dichloro-4-trifluoromethylphenyl)-pyrazole of melting point 211° C. are obtained.

Example 3

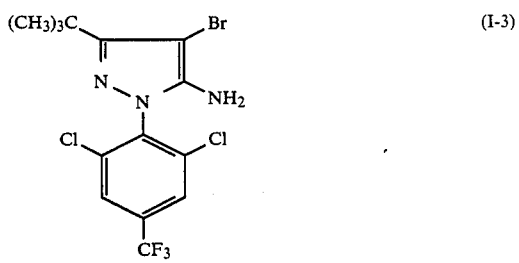
(I-3)

(Process a)

8 g (0.05 mole) of bromine, dissolved in 20 ml of absolute chloroform, are added dropwise to 17.6 g (0.05 mole) of 3-tert.-butyl-5-amino-1-(2,6-dichloro-4-trifluoromethylphenyl)-pyrazole in 50 ml of absolute chloroform at room temperature. The mixture is stirred for a few hours at room temperature, the reaction mixture is concentrated, and the residue is recrystallized from a little methanol.

20.9 g (97% of theory) of 3-tert.-butyl-4-bromo-5-amino-1-(2,6-dichloro-4-trifluoromethylphenyl)-pyrazole of melting point 228°-231° C. are obtained.

Example 4

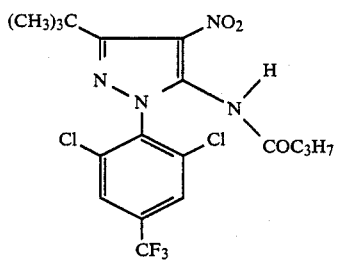

(I-4)

(Process c—α)

4 g (0.01 mole) of 5-amino-3-tert.-butyl-4-nitro-1-(2,6-dichloro-4-trifluoromethylphenyl)-pyrazole, 1.6 g (0.015 mole) of butyryl chloride, 2 drops of concentrated sulphuric acid and 40 ml of butyric acid are stirred for 2 hours at room temperature and for a further 12 hours at 40° C. When the reaction is complete, methylene chloride is added, and the organic phase is washed twice with 2N sodium hydroxide solution and once with water, and dried over magnesium sulphate, and the solvent is removed in vacuo.

After trituration with petroleum ether, 1.5 g (32% of theory) of 3-tert.-butyl-5-butyramido-4-nitro-1-(2,6-dichloro-4-trifluoromethylphenyl)-pyrazole of melting point 152°-154° C. are obtained.

Example 5

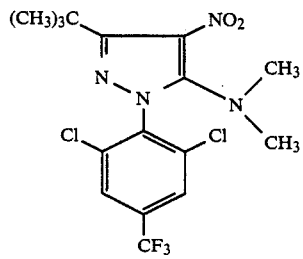

(I-5)

(Process c—β)

7.9 g (0.02 mole) of 5-amino-3-tert.-butyl-4-nitro-1-(2,6-dichloro-4-trifluoromethylphenyl)-pyrazole are dissolved in 160 ml of methylene chloride, and 40 ml of 45% strength aqueous sodium hydroxide solution, a spatula tip of tributylbenzylammonium chloride and 7.6 g (0.06 mole) of dimethyl sulphate are added successively, and the mixture is stirred for 16 hours at room temperature. The aqueous phase is separated off, and the organic phase is washed with water and freed of solvent in vacuo. The residue is taken up in 200 ml of ethanol, 20 ml of 25% strength aqueous ammonia are added, and the mixture is stirred for 6 hours. The solvent is then removed in vacuo, the residue is dissolved in 80 ml of methylene chloride, and the organic phase is washed successively with aqueous ammonium, chloride solution and sodium chloride solution, dried over magnesium sulphate and concentrated in vacuo.

6.9 g (81% of theory) of 3-tert.-butyl-5-dimethylamino-4-nitro-1-(2,6-dichloro-4-trifluoromethylphenyl)-pyrazole of melting point 81°-83° C. are obtained.

Example 6

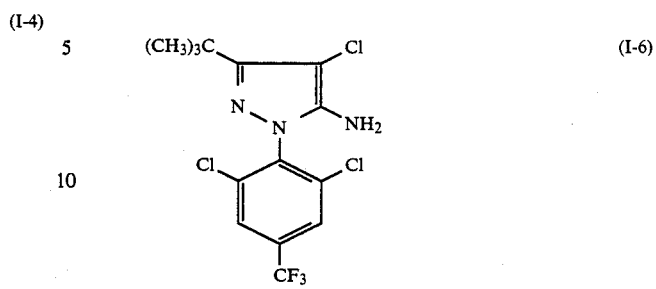

(I-6)

(Process d)

52.8 g (0.12 mole) of 3-tert.-butyl-4-chloro-5-acetamido-1-(2,6-dichloro-4-trifluoromethylphenyl)-pyrazole are refluxed for 8 hours in 250 ml of ethanol and 60 ml of concentrated hydrochloric acid. The reaction mixture is concentrated, taken up in methylene chloride and rendered alkaline using 10% strength sodium hydroxide solution. The organic phase is washed with saturated sodium chloride solution, dried over magnesium sulphate, concentrated and triturated with petroleum ether.

43.2 g (93% of theory) of 3-tert.-butyl-4-chloro-5-amino-1-(2,6-dichloro-4-trifluoromethylphenyl)-pyrazole of melting point 137° C. are obtained.

Example 7

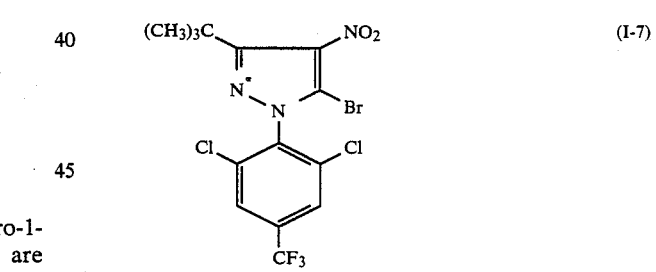

(I-7)

(Process e)

3.6 ml (0.03 mole) of tert.-butyl nitrite are added to 7.9 g (0.02 mole) of 3-tert.-butyl-4-nitro-5-amino-1-(2,6-dichloro-4-trifluoromethylphenyl)-pyrazole in 50 ml of bromoform at room temperature. During this, the temperature increases to 40°-50° C. The reaction mixture is stirred for a few more hours and subsequently concentrated, finally in a high vacuum. The residue is purified by column chromatography over silica gel with the eluent petroleum ether:ethyl acetate (9:1).

4.9 g (53% of theory) of 3-tert.-butyl-4-nitro-5-bromo-1-(2,6-dichloro-4-trifluoromethylphenyl)-pyrazole of melting point 105°-108° C. are obtained.

Example 8

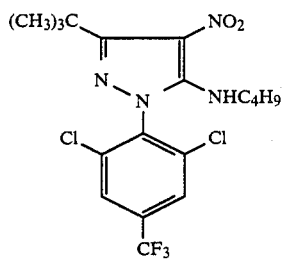

(I-8)

(Process b)

6 g (0.013 mole) of 3-tert.-butyl-4-nitro-5-bromo-1-(2,6-dichloro-4-trifluoromethylphenyl)-pyrazole are placed in 10 ml of n-butylamine. The reaction mixture is first stirred for 4 hours at room temperature and subsequently for 16 hours at 40° C. When the reaction is complete, the reaction solution is poured into 200 ml of water and extracted with methylene chloride. The organic phase is washed with 1N hydrochloric acid with water, dried and concentrated. The residue is purified by column chromatography over silica gel with the eluent petroleum ether:ethyl acetate (9:1).

3.6 g (61% of theory) of 3-tert.-butyl-5-n-butylamino-4-nitro-1-(2,6-dichloro-4-trifluoromethylphenyl)-pyrazole of melting point 84°–85° C. are obtained.

The following substituted 1-aryl-3-tert.-butyl-pyrazoles of the general formula (I) are obtained in a corresponding fashion and according to the general instructions for the preparation:

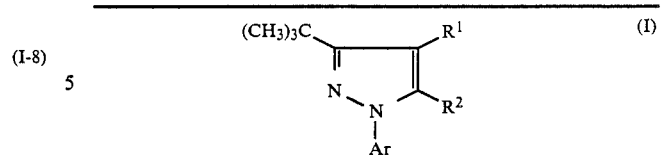

| Ex. No. | R¹ | R² | Ar | Physical data |
|---|---|---|---|---|
| I-9 | NO₂ | —NH₂ | 2,6-Cl₂-4-CF₃-C₆H₂ | m.p. 168°–71° C. |
| I-10 | Cl | H | 2,6-Cl₂-4-CF₃-C₆H₂ | ¹H NMR (in CDCl₃) t-bu: 1.46 ppm (9H,s) 5-pyraz.-H: 7.5 ppm (1H,s) |
| I-11 | Cl | —N(CH₃)₂ | 2,6-Cl₂-4-CF₃-C₆H₂ | m.p. 79°–80° C. |
| I-12 | NO₂ | Cl | 2,6-Cl₂-4-CF₃-C₆H₂ | m.p. 114° C. |
| I-13 | Br | H | 2-Cl-4-CF₃-C₆H₃ | $n_D^{23}$: 1.5340 |
| I-14 | Br | H | 3,5-Cl₂-4-CF₃-C₆H₂ | $n_D^{23}$: 1.5314 |
| I-15 | Cl | H | 2-Cl-4-CF₃-C₆H₃ | $n_D^{23}$: 1.5195 |
| I-16 | Cl | H | 2,6-Cl₂-4-CF₃-C₆H₂ | m.p. 89°–90° C. |
| I-17 | Br | Cl | 2,6-Cl₂-4-CF₃-C₆H₂ | m.p. 88°–89° C. |
| I-18 | Br | NH₂ | C₆H₅ | $n_D^{20}$: 1.5908 |
| I-19 | Br | NH₂ | 2-Cl-C₆H₄ | $n_D^{20}$: 1.6008 |
| I-20 | Br | NH₂ | 3,4-Cl₂-C₆H₃ | m.p. 71°–73° C. |
| I-21 | Br | NH₂ | 4-CH₃-C₆H₄ | m.p. 35°–40° C. |
| I-22 | Br | NH₂ | 4-Cl-C₆H₄ | m.p. 84°–86° C. |
| I-23 | Br | NH₂ | 2-Cl-C₆H₄ | m.p. 79°–83° C. |
| I-24 | Br | H | C₆H₅ | $n_D^{20}$: 1.5778 |
| I-25 | Br | H | 2-Cl-C₆H₄ | $n_D^{20}$: 1.6043 |

-continued

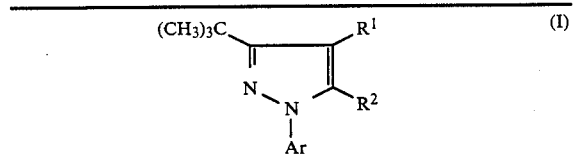

| Ex. No. | R¹ | R² | Ar | Physical data |
|---|---|---|---|---|
| I-26 | Br | H | 3,4-dichlorophenyl | $n_D^{20}$: 1.6158 |
| I-27 | Br | H | 4-chlorophenyl | $n_D^{20}$: 1.5913 |
| I-28 | Br | H | 2-chlorophenyl | m.p. 52°–53° C. |
| I-29 | NO₂ | NH₂ | phenyl | m.p. 164°–165° C. |
| I-30 | Cl | NH₂ | phenyl | $n_D^{20}$: 1.5749 |
| I-31 | Cl | NH₂ | 2-chlorophenyl | $n_D^{20}$: 1.5836 |
| I-32 | Cl | NH₂ | 3,4-dichlorophenyl | m.p. 81°–82° C. |
| I-33 | Cl | NH₂ | 4-methylphenyl | m.p. 78°–80° C. |
| I-34 | Cl | NH₂ | 4-chlorophenyl | m.p. 88°–90° C. |
| I-35 | Cl | NH₂ | 4-methoxyphenyl | m.p. 105°–106° C. |
| I-36 | Cl | NH₂ | 2-chlorophenyl | m.p. 102°–103° C. |
| I-37 | NO₂ | NH₂ | 3-chlorophenyl | m.p. 125°–126° C. |
| I-38 | NO₂ | NH₂ | 3,4-dichlorophenyl | m.p. 149° C. |
| I-39 | NO₂ | NH₂ | 4-methylphenyl | m.p. 158°–160° C. |
| I-40 | NO₂ | NH₂ | 4-chlorophenyl | m.p. 178°–179° C. |
| I-41 | NO₂ | NH₂ | 4-methoxyphenyl | m.p. 116°–117° C. |

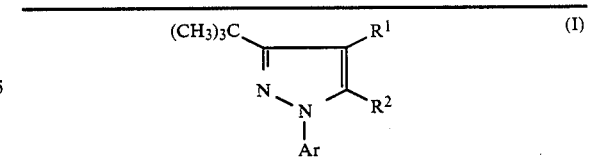

| Ex. No. | R¹ | R² | Ar | Physical data |
|---|---|---|---|---|
| I-42 | NO₂ | NH₂ | 2-chloro-6-methylphenyl | m.p. 219°–220° C. |

Preparation of further starting materials of the formula (II)

Example a

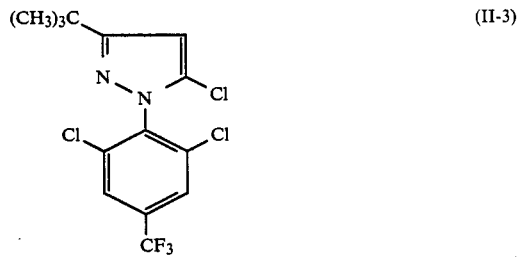

10 g (0.028 mole) of 1-(2,6-dichloro-4-trifluoromethylphenyl)-3-tert.-butyl-5-pyrazolone in 26.1 ml (0.28 mole) of phosphorus oxychloride are heated overnight at 160° C. in a Carius tube under their own pressure. The reaction mixture is subsequently discharged carefully into ice water and extracted with methylene chloride. The organic phase is washed with 12% ammonia solution and saturated sodium chloride solution, dried over magnesium sulphate and concentrated.

8.3 g (80% of theory) of 5-chloro-1-(2,6-dichloro-4-trifluoromethylphenyl)-3-tert.-butylpyrazole are obtained.

¹H NMR (90 MHz/CDCl₃: δ=1.33 (9H, s, C(CH₃)₃); 6.31 (1H, s, 4-pyrazole-H); 7.72 (2H, d, aryl-H) ppm.

Preparation of the precursor

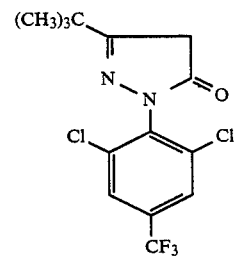

47.4 g (0.3 mole) of methyl 4,4-dimethyl-3-oxo-pentanoate and 73.5 g (0.3 mole) of 2,6-dichloro-4-trifluoromethylphenyl hydrazine and 0.5 g of p-toluenesulphonic acid in 300 ml of toluene are refluxed overnight on a water separator. The solvent is subsequently removed by distillation and the residue is triturated with petroleum ether and filtered off under suction.

96 g (91% of theory) of 1-(2,6-dichloro-4-tri-fluoromethylphenyl)-3-tert.-butyl-5-pyrazolone of melting point 175° C. are obtained.

Example b

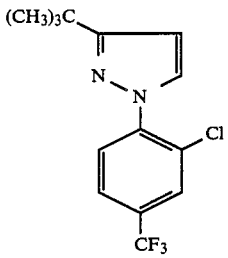

(II-4)

42 g (0.2 mole) of 2-chloro-4-trifluoromethylphenyl hydrazine and 30 g (0.2 mole) of 1,1,1-trimethyl-2-butanone 4,4-dimethylacetal are dissolved in 400 ml of ethanol. The mixture is subsequently stirred for 4 hours at 60° C. and for a further 6 hours at the reflux temperature. 4 ml of concentrated sulphuric acid are then added, and the mixture is stirred overnight at 60° C. When the reaction is complete, the solvent is removed by distillation and the residue is taken up in methylene chloride, washed with saturated sodium hydrogen carbonate solution and water, dried over magnesium sulphate and concentrated.

49 g (81% of theory) of 3-tert.-butyl-1-(2-chloro-4-trifluoromethylphenyl)-pyrazole of refractive index $n_D^{23} = 1.5070$ are obtained.

The following precursors of the formula (II) are obtained corresponding to Preparation Examples 1 and a and b and according to the general instructions for the preparation:

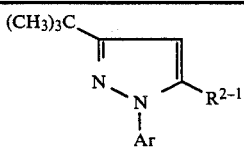

(II)

| Ex. No. | $R^{2-1}$ | Ar | Physical data |
|---|---|---|---|
| II-5 | —NHCOCH$_3$ | ![Cl, Cl, CF3 phenyl] | m.p.: 165–71° C. |
| II-6 | H | ![Cl, Cl, CF3 phenyl] | $n_D^{20}$: 1.5082 |
| II-7 | NH$_2$ | ![phenyl] | m.p. 48°–50° C. |

Use examples

In the following use examples, the compounds shown below were employed as comparison compounds:

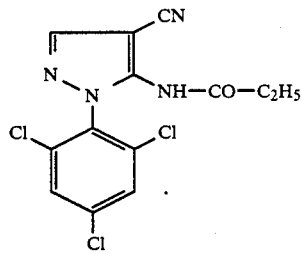

(A)

4-Cyano-5-propionylamino-1-(2,4,6-trichlorophenyl)-pyrazole (known from DE-OS (German Published Specification) No. 3,226,513)

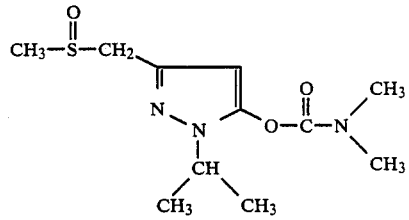

(B)

5-dimethylaminocarbonyloxy-1-isopropyl-3-methylsulphinylmethylpyrazole (known from DE-OS (German Published Specification) No. 2,819,932)

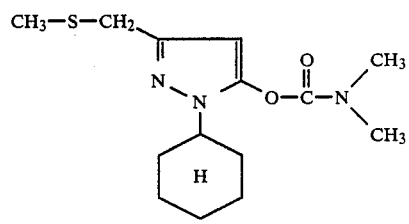

(C)

1-Cyclohexyl-5-dimethylaminocarbonyloxy-3-methylthiomethylpyrazole (known from DE-OS (German Published Specification) No. 2,839,270).

Example A

Phaedon Larvae test

Solvent: 7 parts by weight of dimethylformamide
Emulsifier: 1 part by weight of alkylaryl polyglycol ether To produce a suitable preparation of active compound, 1 part by weight of active compund is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with mustard beetle larvae (Phaedon cochleariae), as long as the leaves are still moist.

After the specified periods of time, the destruction in % is determined. 100% means that all the bettle larvae have been killed; 0% means that none of the beetle larvae have been killed.

In this test, the following compounds of the preparation examples, for example, exhibit a superior activity compared to the prior art: I-6, I-3, I-7, I-9 and I-1.

Example B

Tetranychus test (resistant)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified periods of time, the destruction in % is determined. 100% means that all the spider mites have been killed; 0% means that none of the spider mites have been killed.

In this test, the following compound of the preparation examples, for example, exhibits a superior activity compared to the prior art: I-7.

Example C $LT_{100}$ test for Diptera

Test insects: *Musca domestica*
Number of test insects: 25
Solvent: Acetone 2 parts by weight of active compound are taken up in 1,000 parts by volume of solvent. The solution thus obtained is diluted with further solvent to the desired lower concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per m² of filter paper varies, depending on the concentration of the active compound solution. The stated number of test insects is then introduced into the Petri dish, and the dish is covered with a glass lid.

The condition of the test insects is checked continuously. The time required for a 100% knock-down effect is determined.

In this test, the following compounds of the preparation examples, for example, exhibit superior activity compared to the prior art: I-6 and I-10.

Example D $LD_{100}$ test

Test insects: *Sitophilus granarius*
Number of test insects: 25
Solvent: Acetone 2 parts by weight of active compound are taken up in 1,000 parts by volume of solvent. The solution thus obtained is diluted with further solvent to the desired concentrations.

2.5 ml of the active compound solution are pipetted into a Petri dish. A filter paper disc of about 9.5 cm diameter is located on the bottom of the Petri dish. The Petri dish is left standing open until the solvent has completely evaporated. The amount of active compound per m² of filter paper varies, depending on the concentration of the active compound solution. The stated number of test insects is then introduced into the Petri dish, and the dish is covered with a glass lid.

The condition of the test insects is checked 3 days after the experiments have been set up. The destruction in % is determined. In this test, the following compounds of the preparation examples, for example, exhibit superior activity compared to the prior art: I-9, I-6 and I-10.

EXAMPLE E $LD_{100}$ test

Test insects: *Blatella germanica*
Number of test insects: 25
Solvent: Acetone 2 parts by weight of active compound are taken up in 1,000 parts by volume of solvent. The solution thus obtained is diluted with further solvent to the desired concentrations.

2.5 ml of the active compound solution are pipetted into a Petri dish. A filter paper disc of about 9.5 cm diameter is located on the bottom of the Petri dish. The Petri dish is left standing open until the solvent has completely evaporated. The amount of active compound per m² of filter paper varies, depending on the concentration of the active compound solution. The stated number of test insects is then introduced into the Petri dish, and the dish is covered with a glass lid.

The condition of the test animals is checked 3 days after the experiments have been set up. The destruction in % is determined. In this test, the following compounds of the preparation examples, for example, exhibit superior activity compared to the prior art: I-6, I-10 and I-7.

EXAMPLE F

Test with *Stomoxys calcitrans*

Emulsifier: 35 parts by weight of ethylene glycol monomethyl ether
35 parts by weight of nonylphenol polyglycol ether To produce a suitable preparation of active compound, three parts by weight of active compound are mixed with seven parts by weight of the solvent mixture indicated above, and the concentrate thus obtained is diluted with water to the particular desired concentration.

10 adult *Stomoxys calcitrans* are placed in Petri dishes containing filter paper discs of appropriate size which were saturated one day before the start of the experiment with 1 ml of the active compound preparation to be tested. After 3 hours, the degree of destruction is determined.

In this test, the following compound of the preparation examples, for example, exhibits superior action compared to the prior art: I-3.

EXAMPLE G

Facefly test (*Musca autumnalis*)

Solvent: 35 parts by weight of ethylene glycol monomethyl ether
35 parts by weight of nonylphenol polyglycol ether To produce a suitable formulation, three parts by weight of active compound are mixed with seven parts of the abovementioned solvent/emulsifier mixture and the emulsion concentrate thus obtained is diluted with water to the particular desired concentration.

10 adult faceflies (*Musca autumnalis*) are introduced into Petri dishes containing filter paper discs of appropriate size which have been impregnated one day before the start of the test with 1 ml of the active compound preparation to be tested. After 3 hours, the degree of destruction is determined in percent, 100% meaning that all of the flies have been destroyed and 0% meaning that no flies have been destroyed.

In this test, the following compound of the preparation examples, for example, exhibits a superior action compared to the prior art: I-3.

It is understood that the specification and examples are illustrated but not limitative of the present invention and that other embodiments within the spirit and scope of the invention will suggest themselves to those skilled in the art.

We claim:

1. A 1-aryl-3-tert.-butylpyrazole of the formula

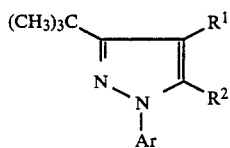

in which
$R^1$ represents nitro or halogen,
$R^2$ represents halogen or the $-NR^3R^4$ group, and also may represent hydrogen when $R^1$ is halogen, where
$R^3$ represents hydrogen or, in each case straight-chain or branched, alkyl, alkenyl and alkinyl, in each case having up to 8 carbon atoms, which are optionally monosubstituted or polysubstituted, where the substituents are identical or different selected from halogen, cyano, nitro, hydroxyl, mercapto, carboxyl, straight-chain or branched alkoxy, alkylthio and alkoxycarbonyl, in each case having up to 6 carbon atoms; furthermore $R^3$ represents cycloalkyl having 3 to 7 carbon atoms and cycloalkylalkyl having 3 to 7 carbon atoms in the cycloalkyl part and 1 to 4 carbon atoms in the alkyl part optionally substituted in the cycloalkyl part by halogen and straight-chain or branched alkyl having 1 to 4 carbon atoms; and
$R^4$, independently of $R^3$, represents the same radicals as $R^3$, and, in addition, a

radical, where
X represents oxygen or sulphur, and
$R^5$ represents hydrogen, straight-chain or branched alkyl having 1 to 12 carbon atoms, straight-chain or branched alkenyl or alkinyl, in each case having 2 to 4 carbon atoms, straight-chain or branched alkoxyalkyl, alkylthioalkyl, alkoxy, alkylthio, alkylamino, dialkylamino or halogenoalkyl in each case having 1 to 4 carbon atoms in the individual alkyl parts and, in the case of halogenoalkyl, having up to 9 identical or different halogen atoms, in addition $R^5$ may be cycloalkyl, having 3 to 7 carbon atoms, which is optionally monosubstituted or polysubstituted by halogen, $C_1-C_4$-alkyl or $C_1-C_4$-halogenoalkyl, the substituents being identical or different, and $R^5$ may be phenyl, phenoxy, phenylthio or phenylamino which is in each case optionally substituted on the phenyl by halogen, straight-chain or branched alkyl or alkoxy in each case having 1 to 4 carbon atoms, or halogenoalkyl having 1 to 4 carbon atoms and 1 to 9 identical or different halogen atoms; and Ar represents phenyl, 2-pyridyl, 3-pyridyl or 4-pyridyl which is in each case optionally monosubstituted or polysubstituted, the substituents being identical or different and selected from halogen, cyano, nitro, straight-chain or branched alkyl, alkoxy or alkoxycarbonyl in each case having 1 to 4 carbon atoms in the alkyl parts, straight-chain or branched halogenoalkyl or halogenoalkoxy in each case having 1 to 4 carbon atoms and 1 to 9 identical or different halogen atoms, or an $-S(O)_m-R^6$ radical,
where
$R^6$ repesents amino, straight-chain or branched alkyl, alkylamino, dialkylamino or halogenoalkyl in each case having 1 to 4 carbon atoms in the individual alkyl parts, and in the case of halogenoalkyl, having 1 to 9 identical or different halogen atoms, and
m represents a number 0, 1 or 2,
with the proviso that Ar is not dinitrophenyl.

2. A 1-aryl-3-tert.-butyl-pyrazole according to claim 1, in which
$R^1$ represents nitro, chlorine or bromine;
$R^2$ represents chlorine, bromine or the $-NR^3R^4$ group; and also may represent hydrogen when $R^1$ represents a halogen, where
$R^3$ represents methyl, ethyl, n- or i-propyl, n-, i-, s- or t-butyl, allyl, butenyl, propargyl or butinyl which is in each case optionally mono- or trisubstituted, the substituents being identical or different and selected from fluorine, chlorine, bromine, iodine, cyano, nitro, hydroxyl, mercapto, carboxyl, methoxy, ethoxy, n- or i-propoxy, methylthio, ethylthio, n- or i-propylthio, methoxycarbonyl, ethoxycarbonyl, n- or i-propoxycarbonyl and n-, i-, s- or t-butoxy-carbonyl; or $R^3$ furthermore represents cyclopropyl, cyclopropylmethyl, cyclopentyl, cyclopentylmethyl, cyclohexyl, cyclohexylmethyl, cyclohexylethyl, cycloheptyl or cycloheptylmethyl which is in each case optionally mono- to trisubstituted in the cycloalkyl part, the substituents being identical or different and being selected from the group consisting of halogen and straight-chain or branched alkyl having 1 to 4 carbon atoms;
$R^4$, independently of $R^3$, represents the same radicals as $R^3$, and, in addition, a

radical where
X represents oxygen or sulphur, and
$R^5$ represents hydrogen, methyl, ethyl, n- or i-propyl, n-, i-, s- or t-butyl, undecyl, vinyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 3-chloropropyl or heptafluoro-n-propyl, or $R^5$ represents cyclopropyl, cyclopentyl or cyclohexyl which is in each case optionally mono- to tetrasubstituted by fluorine, chlorine, bromine, methyl or trifluoromethyl, the substituents being identical or different, or $R^5$ represents phenyl, phenoxy, phenylthio or phenylamino which is in each case optionally mono- to trisubstituted by methyl, methoxy, chlorine or trifluoromethyl, the substituents being being identical or different; and Ar represents phenyl which is optionally mono- to pentasubstituted the substituents being identical or different, or Ar represents 2-pyridyl, 3-pyridyl or 4-pyridyl, which is in each case optionally mono- to tetrasubstituted, the substituents being identical or different said substituents being in each case: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an $—S(O)_m—R^6$ radical, where $R^6$ represents amino, methylamino, ethylamino, dimethylamino, diethylamino, fluorodichloromethyl, difluoromethyl, tetrafluoroethyl, trichloroethyl, trifluoromethyl, difluorochloromethyl, methyl or ethyl and m represents a number 0, 1 or 2, with the proviso that Ar is not dinitrophenyl.

3. A 1-aryl-3-tert.-butyl-pyrazole according to claim 1, in which $R^1$ represents nitro, fluorine, chlorine, bromine or iodine; and $R^2$ represents fluorine, chlorine, bromine, iodine or the $—NR^3R^4$ group; and also may represent hydrogen when $R^1$ represents a halogen.

4. A 1-aryl-3-tert.-butyl-pyrazole according to claim 1, wherein such pyrazole is 3-tert.-butyl-4-nitro-5-propionamido-1-(2,6-dichloro-4-trifluoromethylphenyl)-pyrazole of the formula

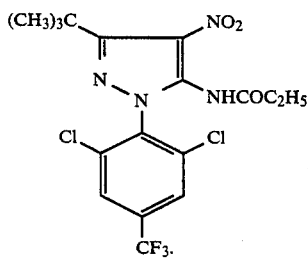

5. A 1-aryl-3-tert.-butyl-pyrazole according to claim 1, wherein such pyrazole is 3-tert.-butyl-4-bromo-5-amino-1-(2,6-dichloro-4-trifluoromethylphenyl)-pyrazole of the formula

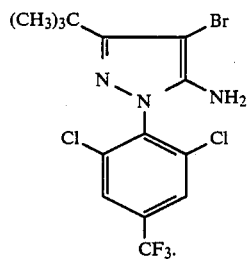

6. A 1-aryl-3-tert.-butyl-pyrazole according to claim 1, wherein such pyrazole is 3-tert.-butyl-4-chloro-5-amino-1-(2,6-dichloro-4-trifluoromethylphenyl)-pyrazole of the formula

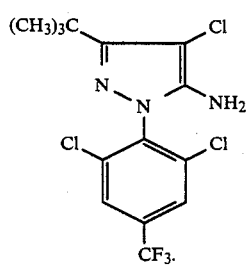

7. A 1-aryl-3-tert.-butyl-pyrazole according to claim 1, wherein such pyrazole is 3-tert.-butyl-4-nitro-5-bromo-1-(2,6-dichloro-4-trifluoromethylphenyl)-pyrazole of the formula

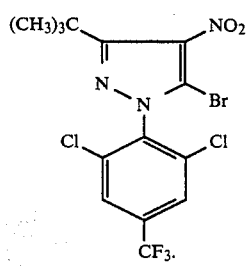

8. A 1-aryl-3-tert.-butyl-pyrazole according to claim 1, wherein such pyrazole is 3-tert.-butyl-4-nitro-5-amino-1-(2,6-dichloro-4-trifluoromethylphenyl)-pyrazole of the formula

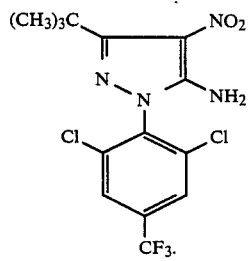

9. A 1-aryl-3-tert.-butyl-pyrazole according to claim 1, wherein such pyrazole is 3-tert.-butyl-4-chloro-1-(2,6-dichloro-4-trifluoromethylphenyl)-pyrazole of the formula

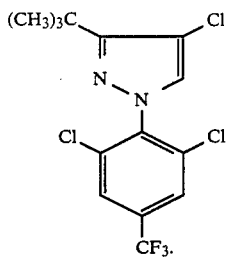

10. An insecticidal or acaricidal composition comprising an insecticidally or acaricidally effective amount of a compound according to claim 1 and a carrier.

11. A method of combating insects or acarids which comprises applying to such insects, acarids or a habitat thereof an insecticidally or acaricidally effective amount of a compound according to claim 1 and a carrier.

12. The method according to claim 11, wherein such compound is
3-tert.-butyl-4-nitro-5-propionamido-1-2,6-dichloro-4-trifluoromethylphenyl)-pyrazole,
3-tert.-butyl-4-bromo-5-amino-1-(2,6-dichloro-4-trifluoromethylphenyl)-pyrazole,
3-tert.-butyl-4-chloro-5-amino-1-(2,6-dichloro-4-trifluoromethylphenyl)-pyrazole,
3-tert.-butyl-4-nitro-5-bromo-1-(2,6-dichloro-4-trifluoromethylphenyl)-pyrazole,
3-tert.-butyl-4-nitro-5-amino-1-(2,6-dichloro-4-trifluoromethylphenyl)-pyrazole or
3-tert.-butyl-4-chloro-1-(2,6-dichloro-4-trifluoromethylphenyl)-pyrazole.

* * * * *

UNITED STATES PATENT AND TRADEMARK OFFICE
CERTIFICATE OF CORRECTION

PATENT NO. : 4,826,867

DATED : May 2, 1989

INVENTOR(S) : Uta Jensen-Korte, et al

It is certified that error appears in the above-identified patent and that said Letters Patent is hereby corrected as shown below:

Abstract, line 14 — Delete "$R^31$" and substitute --$R^3$--

Title Page, under "Foreign Patent Documents, line 2 — Delete "European Pat. Off." and substitute --Fed. Rep. of Germany--

Col. 4, line 12 — Delete "(a)" and substitute --($\alpha$)--

Col. 14, line 64 — Delete "CO'O" and substitute --CO-O--

Col. 16, line 47 — Delete "hydrocarbon" and substitute --hydrocarbons--

Col. 18, line 27 — Delete "acid" and substitute --acids--

Col. 18, line 33 — Delete "case" and substitute --cases--

Col. 18, line 40 — Delete "-°°C." and substitute -- -20°C.--

Col. 19, line 1 — Delete "specie" and substitute --species--

Col. 19, line 56 — Correct spelling of --cochleariae--

Col. 21, line 43 — After "possible" delete "for" and substitute --to--

Col. 22, line 21 — Delete "liffe" and substitute --life--

Col. 32, line 31 — Delete "dimethylaminocarbonyloxy" and substitute --Dimethylaminocarbonyloxy--

UNITED STATES PATENT AND TRADEMARK OFFICE
CERTIFICATE OF CORRECTION

PATENT NO. : 4,826,867

DATED : May 2, 1989

INVENTOR(S) : Uta Jensen-Korte, et al

It is certified that error appears in the above-identified patent and that said Letters Patent is hereby corrected as shown below:

Col. 36, line 20   Correct spelling of --represents--

Col. 36, line 35   After "mono-" delete "or" and substitute --to--

Signed and Sealed this

Twenty-eighth Day of April, 1992

Attest:

HARRY F. MANBECK, JR.

Attesting Officer   Commissioner of Patents and Trademarks